(12) United States Patent
Torrence et al.

(10) Patent No.: US 8,461,379 B2
(45) Date of Patent: Jun. 11, 2013

(54) PRODUCTION OF ACETIC ACID COMPRISING FEEDING AT LEAST ONE REACTANT TO A RECYCLE STREAM

(75) Inventors: G. Paull Torrence, League City, TX (US); Raymond J. Zinobile, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 340 days.

(21) Appl. No.: 12/902,661

(22) Filed: Oct. 12, 2010

(65) Prior Publication Data

US 2012/0088929 A1 Apr. 12, 2012

(51) Int. Cl.
*C07C 51/12* (2006.01)

(52) U.S. Cl.
USPC .......................................................... 562/519

(58) Field of Classification Search
CPC ..................................................... C07C 51/12
See application file for complete search history.

(56) References Cited

U.S. PATENT DOCUMENTS

| | | | |
|---|---|---|---|
| 3,769,329 A * | 10/1973 | Paulik et al. | 560/232 |
| 4,615,806 A | 10/1986 | Hilton | |
| 4,894,477 A | 1/1990 | Scates | |
| 4,994,608 A | 2/1991 | Torrence | |
| 5,001,259 A | 3/1991 | Smith | |
| 5,026,908 A | 6/1991 | Smith | |
| 5,144,068 A | 9/1992 | Smith | |
| 5,696,284 A | 12/1997 | Baker | |
| 5,731,252 A | 3/1998 | Warner | |
| 5,877,347 A | 3/1999 | Ditzel | |
| 5,877,348 A | 3/1999 | Ditzel | |
| 5,883,295 A | 3/1999 | Sunley | |
| 5,932,764 A | 8/1999 | Morris | |
| 5,942,460 A | 8/1999 | Garland | |
| 6,103,934 A * | 8/2000 | Hallinan et al. | 562/517 |
| 6,140,535 A | 10/2000 | Williams | |
| 6,143,930 A | 11/2000 | Singh | |
| 6,225,498 B1 | 5/2001 | Blay | |
| 6,339,171 B1 | 1/2002 | Singh | |
| 6,627,770 B1 | 9/2003 | Cheung | |
| 6,657,078 B2 | 12/2003 | Scates | |
| 6,677,480 B2 * | 1/2004 | Huckman et al. | 562/519 |
| 7,005,541 B2 | 2/2006 | Cheung | |
| 7,223,886 B2 | 5/2007 | Scates | |
| 7,465,823 B2 | 12/2008 | Bhaskaran | |
| 2004/0122257 A1 | 6/2004 | Cheung et al. | |
| 2005/0197506 A1 | 9/2005 | Scates et al. | |
| 2005/0197513 A1 | 9/2005 | Trueba | |
| 2006/0247466 A1 | 11/2006 | Zinobile | |
| 2006/0293537 A1 | 12/2006 | Trueba | |
| 2008/0287706 A1 | 11/2008 | Powell | |
| 2008/0293966 A1 | 11/2008 | Scates | |
| 2009/0107833 A1 | 4/2009 | Warner | |
| 2009/0209786 A1 | 8/2009 | Scates et al. | |
| 2009/0270651 A1 | 10/2009 | Zinobile | |

OTHER PUBLICATIONS

Jones, J. H., "The Cativa Process for the Manufacture of Acetic Acid", Platinum Metals Review, 44 (3), pp. 94-105 (2000).
International Search Report and Written Opinion for PCT/US2011/054576 mailed Feb. 9, 2012 (16 pages).
Eby, et al., "Methanol Carbonylation to Acetic Acid," Applied Industrial Catalysis, vol. 1, Chapter 10, pp. 275-296, ISBN 0-12-440201-1, 1983.
International Preliminary Report on Patentability for PCT/US2011/054576 mailed Jan. 21, 2013.

* cited by examiner

*Primary Examiner* — Paul A Zucker

(57) ABSTRACT

This invention relates to processes for producing acetic acid from carbon monoxide and, in particular, to improved processes, wherein at least one reactant is fed upstream of a reactor recycle pump and/or to a pump-around loop.

13 Claims, 6 Drawing Sheets

PRODUCTION OF ACETIC ACID COMPRISING FEEDING AT LEAST ONE REACTANT TO A RECYCLE STREAM

FIELD OF THE INVENTION

This invention relates to processes for producing acetic acid from carbon monoxide and, in particular, to improved processes, wherein at least one reactant is fed upstream of a reactor recycle pump and/or to a pump-around loop.

BACKGROUND OF THE INVENTION

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "The Cativa™ Process for the Manufacture of Acetic Acid," *Platinum Metals Review*, 44 (3): 94-105, the entire content and disclosure of which is hereby incorporated by reference.

In the production of acetic acid there may be several limits on the capacity of the system. One such limit is the amount of reactants that may be fed to the reactor. Increasing the feed may require increasing the capacity of the pumps to handle the higher throughput. Reconfiguring the piping, foundations, and utilities, as well as the associated reconfiguration downtime, makes changing over to larger-capacity pumps economically unattractive. Also these pumps are typically high pressure pumps which are more expensive.

There remains a need to continue to improve the capacity for producing acetic acid. The present invention provides such a need.

SUMMARY OF THE INVENTION

The present invention relates to processes for producing acetic acid from carbon monoxide and, in particular, to improved processes, wherein at least one reactant is fed upstream of a reactor recycle pump and/or to a pump-around loop. For example, in a first embodiment, a process of the present invention comprises the steps of reacting carbon monoxide with at least one reactant in a reactor containing a reaction medium to produce a reaction product comprising acetic acid; separating the reaction product in a flasher into a liquid recycle stream and a crude product stream comprising acetic acid, the halogen promoter, methyl acetate and water; introducing at least a portion of the liquid recycle stream to the reactor via one or more pumps; and feeding a portion of the reactants upstream of at least one of the one or more pumps; wherein the liquid recycle stream comprises at least one reactant. In some embodiments, the portion of the at least one reactant is fed to a lower portion of the flasher. In other embodiments, the portion of the at least one reactant is fed to the liquid recycle stream.

The reaction medium preferably comprises water, acetic acid, methyl acetate, a halogen promoter, and a catalyst. The reactants preferably are selected from the group consisting of methanol, methyl acetate, methyl formate, dimethyl ether, and mixtures thereof.

In a second embodiment, a process of the present invention comprises the steps of reacting carbon monoxide with at least one reactant in a reactor containing a reaction medium to produce a reaction product comprising acetic acid; separating the reaction product in a flasher into a liquid recycle stream and a crude product stream comprising acetic acid, the halogen promoter, methyl acetate and water; introducing at least a portion of the liquid recycle stream to the reactor via one or more pumps; and feeding a portion of the at least one reactant upstream of at least one of the one or more pumps; wherein the liquid recycle stream comprises the at least one reactant, wherein the process further comprises capturing one or more vapor streams in a vent recovery unit; scrubbing the one or more vapor streams with a scrubbing solvent comprising the at least one reactant to produce a recovery stream; and feeding at least a portion of the recovery stream upstream of at least one of the one or more pumps.

In a third embodiment, a process of the present invention comprises the steps of reacting carbon monoxide with at least one reactant in a reactor containing a reaction medium to produce a reaction product comprising acetic acid; separating the reaction product in a flasher into a liquid recycle stream and a crude product stream comprising acetic acid, the halogen promoter, methyl acetate and water; introducing at least a portion of the liquid recycle stream to the reactor via one or more pumps; and feeding a portion of the at least one reactant upstream of at least one of the one or more pumps; wherein the liquid recycle stream comprises the at least one reactant, wherein the process further comprises withdrawing a portion of the reaction product to a pump-around loop; and feeding another portion of the at least one reactant to the pump-around loop.

In a fourth embodiment, a process of the present invention comprises the steps of reacting carbon monoxide with at least one reactant in a reactor containing a reaction medium to produce a reaction product comprising acetic acid; withdrawing a portion of the reaction product to a pump-around loop; and feeding a portion of the at least one reactant to the pump-around loop.

In a fifth embodiment, a process of the present invention comprises the steps of reacting carbon monoxide with at least one reactant in a reactor containing a reaction medium to produce a reaction product comprising acetic acid; withdrawing a portion of the reaction product to a pump-around loop; and feeding a portion of the at least one reactant to the pump-around loop; wherein the process further comprises capturing one or more vapor streams in a vent recovery unit; scrubbing the one or more vapor streams with a scrubbing solvent comprising the at least one reactant to produce a recovery stream; and feeding at least a portion of the recovery stream to upstream of at least one of the one or more pumps.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1A:
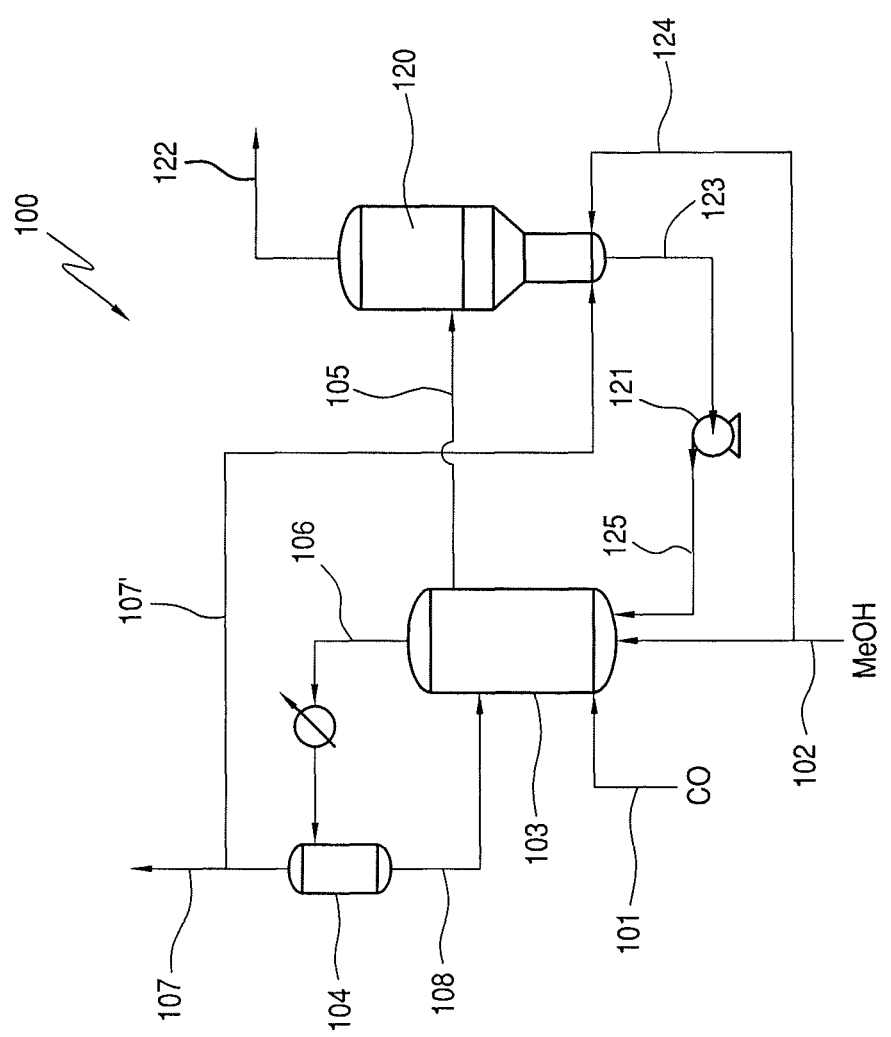
FIG. 1A illustrates an exemplary scheme wherein at least one reactant is fed to a flasher.

The present invention generally relates to producing acetic acid by feeding at least one reactant upstream of a reactor recycle pump and/or to a pump-around loop. The reactants are selected from the group consisting of methanol, methyl acetate, methyl formate, dimethyl ether, and/or mixtures thereof. Preferably the reactant comprises methanol. Upstream of a reactor recycle pump refers to any location prior to the pump that returns a liquid recycle stream to the carbonylation reactor. It should be understood that a carbonylation system may comprise several reactor recycle pumps and the additional reactants may be fed upstream of any of those pumps. Preferably the reactant is fed to a flasher and/or a liquid recycle stream from the flasher. In another embodiment, the reactant may be fed to a pump-around loop. Embodiments of the present invention advantageously allow the reactant to be introduced to the methanol carbonylation process at a location in addition to the carbonylation reactor. While not being bound to one particular theory, the present invention improves the overall production of acetic acid by increasing the amount of available reactants in the carbonylation reactor.

Under steady state operating conditions the amount of reactants that may be fed to the carbonylation reactor may be limited. One potential limitation may be the capacity of the supply pumps for the feed. Thus, although the reactor may have capacity for increased production, it may be difficult to provide the necessary amount of feed. Embodiments of the present invention may increase the total amount of the reactants provided to the carbonylation reactor by introducing reactants at locations other than through the supply feed.

In one embodiment, the source of the reactants may be the fresh reactants that are supplied to the carbonylation reactor. In some embodiments, an additional amount of those fresh reactants may be supplied upstream of a reactor recycle pump. In some embodiments, an additional amount of those fresh reactants may be supplied to a pump-around loop.

In another embodiment of the invention, a vent stream is scrubbed with a scrubbing solvent comprising at least one reactant to recover low boiling point components. Those low boiling point components, along with the scrubbing solvent, form a returned stream. The returned stream may be used as a source of the reactants and fed to a flasher, a liquid recycle stream, and/or to a pump-around loop.

It is believed that, without being bound by theory, adding the at least one reactant in the manner described may reduce certain impurities, such as acetaldehyde and propionic acid, in the crude acetic acid product. A reduction in impurities may further improve separation and purification efficiencies. It is believed that embodiments of the present invention will increase the concentration of methyl acetate in the carbonylation flasher thereby reducing the hydrogen iodide concentration by shifting the reaction of hydrogen iodide with methyl acetate in favor of methyl iodide, as described in Equation 1 below. Accordingly, the reduced hydrogen iodide concentration in the flasher will reduce the formation of acetaldehyde as described in Equation 2 below. The reduction of acetaldehyde in the carbonylation system decreases the formation of impurities such as permanganate reducing compounds (PRC's) and propionic acid.

$$HI + CH_3OAc \rightarrow CH_3I + HOAc \quad \text{Equation 1:}$$

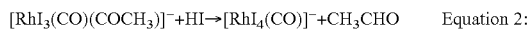
$$[RhI_3(CO)(COCH_3)]^- + HI \rightarrow [RhI_4(CO)]^- + CH_3CHO \quad \text{Equation 2:}$$

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention may be appreciated in connection with, for example, the carbonylation of methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is utilized, the rhodium catalyst may be added in any suitable form such that rhodium is in the catalyst solution as an equilibrium mixture including $[Rh(CO)2I2]-$ anion as is well known in the art. Iodide salts optionally maintained in the reaction mixtures of the processes described herein may be in the form of a soluble salt of an alkali metal or alkaline earth metal or a quaternary ammonium or phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. In some embodiments, the rhodium catalyst concentration in the liquid reaction medium may be in the range of 100 ppm to 6000 ppm. For additional detail regarding rhodium catalysis and iodide salt generation, see U.S. Pat. Nos. 5,001,259; 5,026,908; 5,144,068 and 7,005,541, the entireties of which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H+$, $[Ir(CO)_2I_4]^-H^+$, $[Ir(CH_3)I_3(CO)_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol using iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

A halogen co-catalyst/promoter is generally used in combination with the Group VIII metal catalyst component. Methyl iodide is preferred as the halogen promoter. Preferably, the concentration of halogen promoter in the liquid reaction composition is in the range 1 to 50% by weight, preferably 2 to 30% by weight.

The halogen promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in first reactor 105 is preferably from 150° C. to 250° C., e.g., from 155° C. to 235° C., or from 160° C. to 220° C. The pressure of the carbonylation reaction is from 10 to 200 bar, preferably 10 to 100 bar, and most preferably 15 to 50 bar. Acetic acid is typically manufactured in a liquid phase reaction at a temperature of from about 160 to 220° C. and a total pressure of from about 20 to about 50 bar.

The separation system preferably controls water and acetic acid content in the reactor, as well as throughout the system and, optionally, controls the removal of permanganate reducing compounds (PRC's). PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

Generally, a carbonylation system of the present invention comprises a reaction zone 100 and a purification zone (not shown). FIGS. 1A-3B show an exemplary reaction zone 100 of a carbonylation system for the production of acetic acid in accordance with embodiments of the present invention. Furthermore, additional carbonylation systems that may be used with embodiments of the present invention include those described in U.S. Pat. Nos. 7,223,886, 7,005,541, 6,6657,078, 6,339,171, 5,731,252, 5,144,068, 5,026,908, 5,001,259, 4,994,608, and U.S. Pub. No. 2008/0287706, 2008/0293966, 2009/0107833, 2009/0270651, the entire contents and disclosures of which are hereby incorporated by reference. It should be understood that the reaction zone 100 shown are exemplary and other components may be used within the scope of the present invention.

Figure 1B:
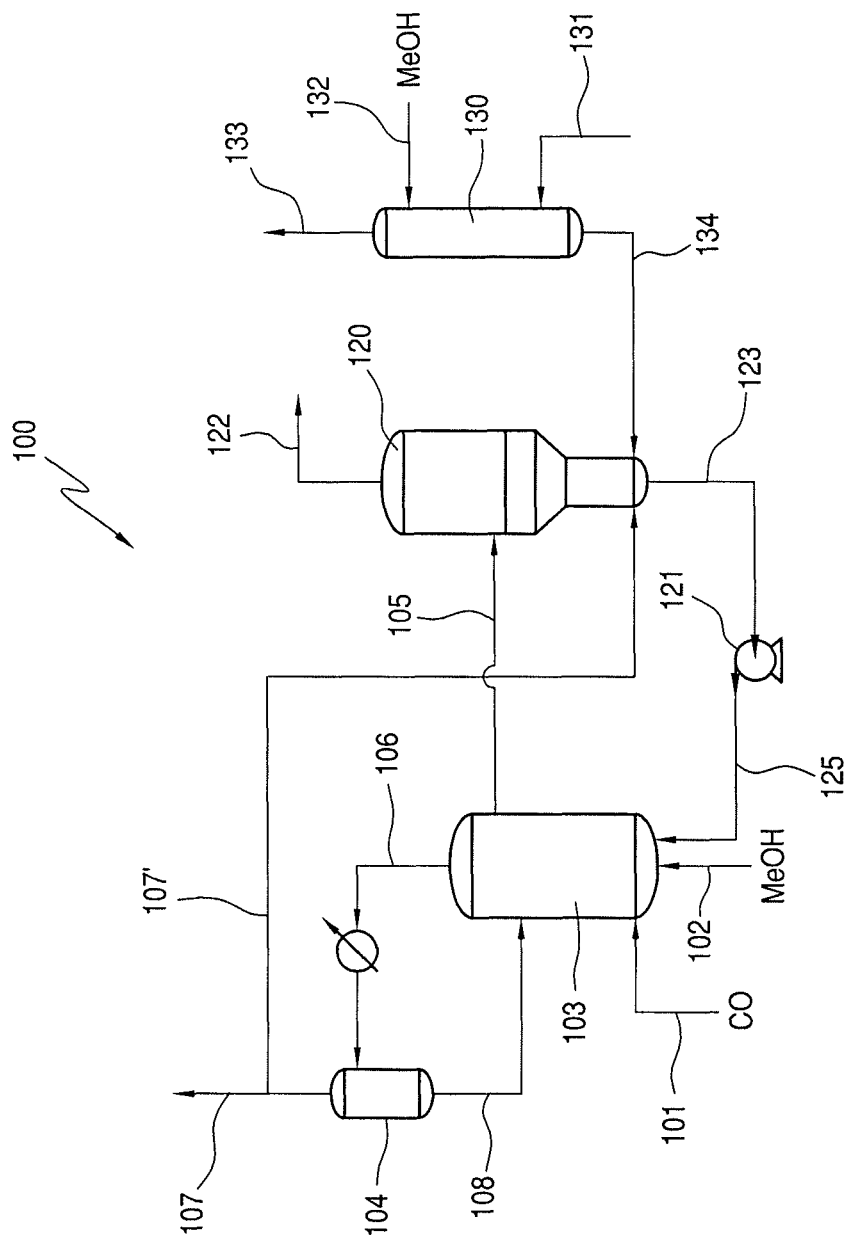
FIG. 1B illustrates an exemplary scheme wherein a recovery stream comprising at least one reactant is fed to a flasher.
Figure 2A:
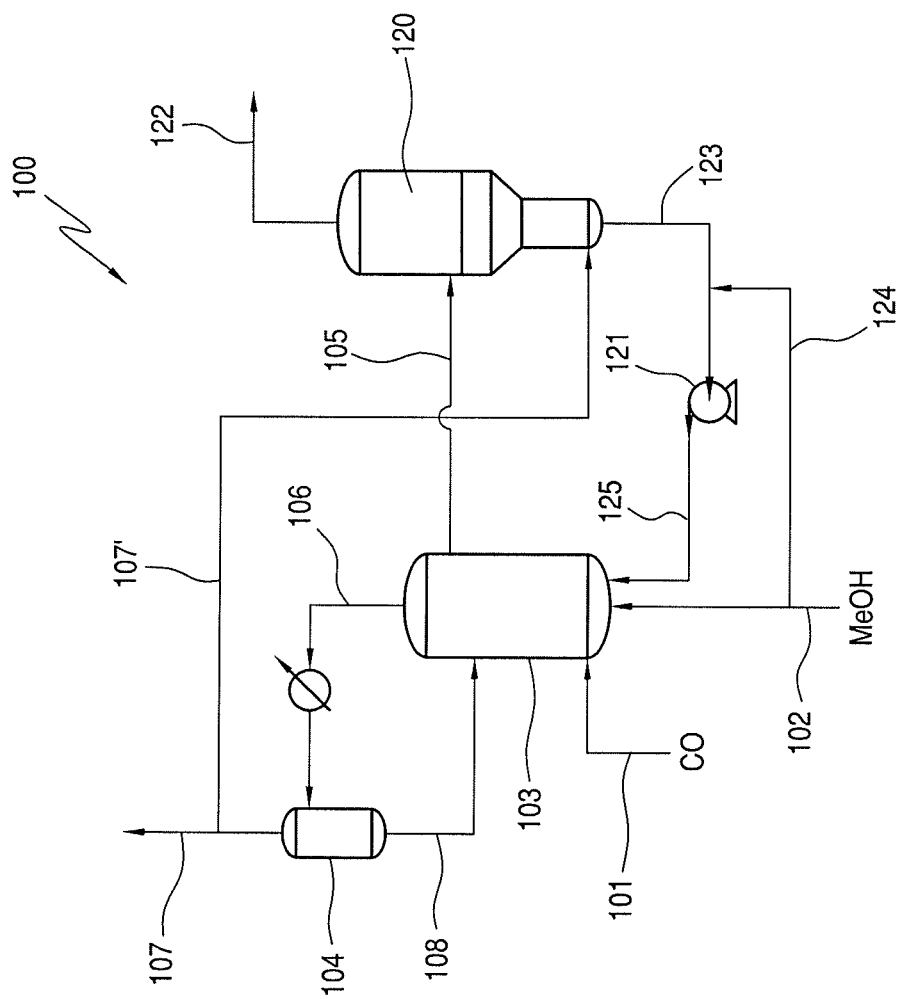
FIG. 2A illustrates an exemplary scheme wherein at least one reactant is fed to a liquid recycle stream.
Figure 2B:
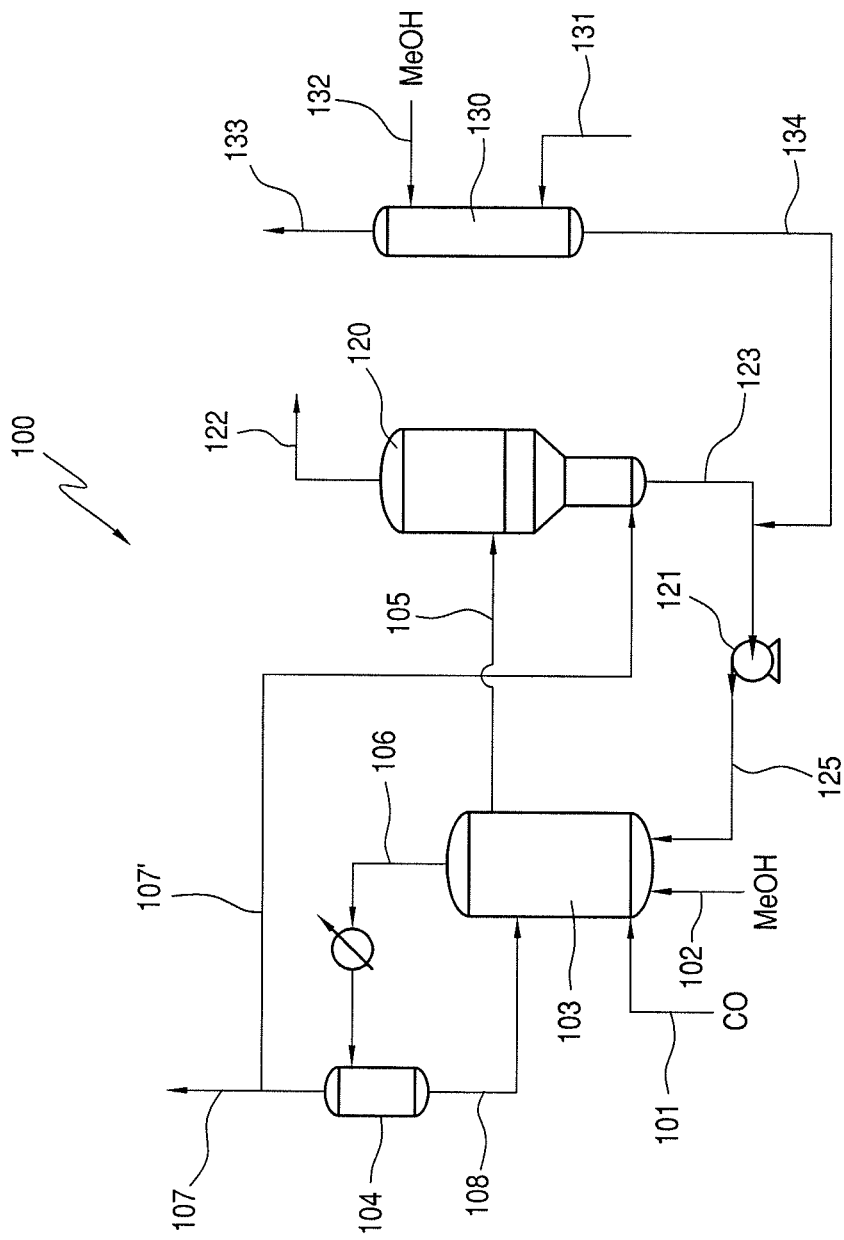
FIG. 2B illustrates an exemplary scheme wherein a recovery stream comprising at least one reactant is fed to a liquid recycle stream.
Figure 3A:
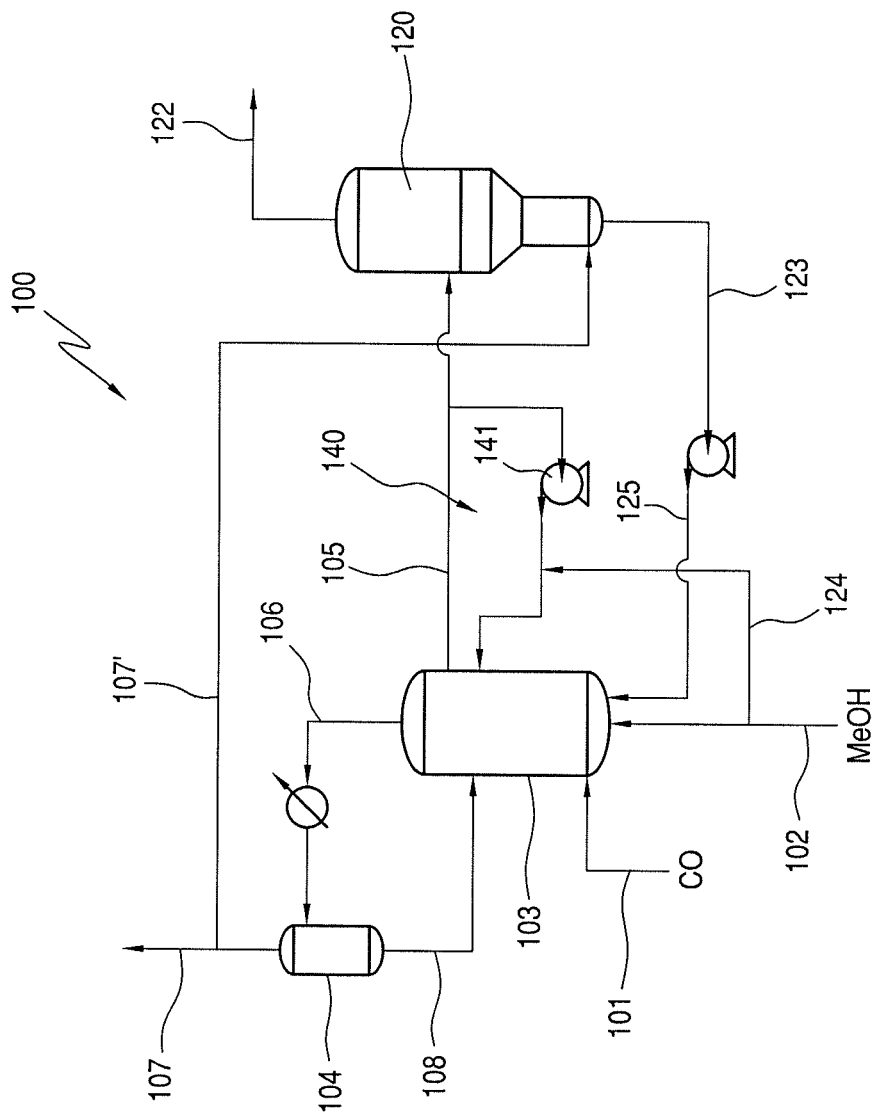
FIG. 3A illustrates an exemplary scheme wherein at least one reactant is fed to a pump-around loop.
Figure 3B:
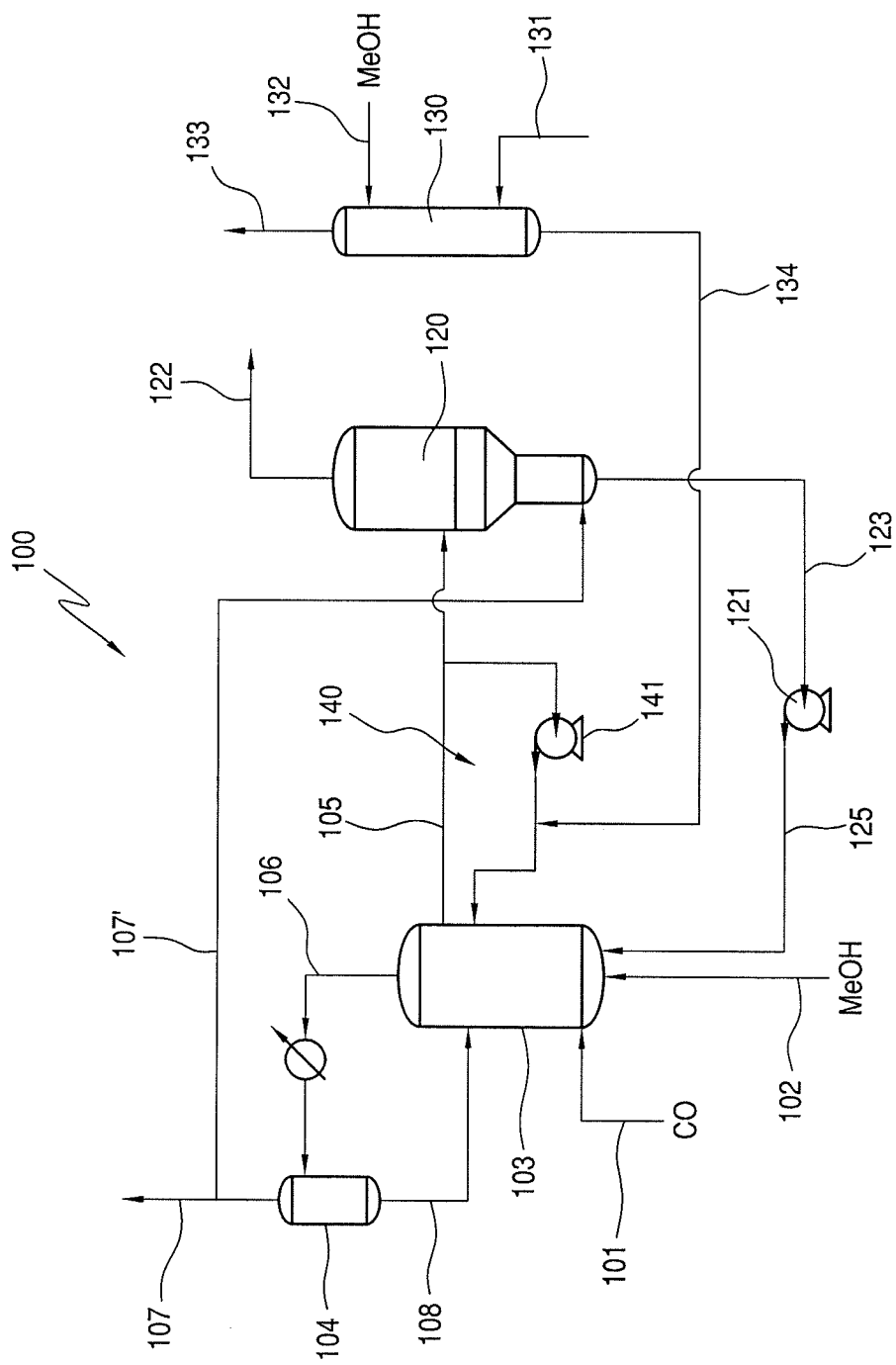
FIG. 3B illustrates an exemplary scheme wherein a recovery stream comprising at least one reactant is fed to a pump-around loop.

Referring to FIGS. 1A and 2A, reaction zone 100 comprises carbon monoxide feed stream 101, reactant feed stream 102, reactor 103, reactor recovery unit 104, flasher 120, and reactor recycle pump 121. In FIGS. 1B, 2B, and 3B, in addition to reaction zone 100, the carbonylation system also comprises vent recovery unit 130, vent stream feed 131, and scrubbing solvent feed 132. In FIGS. 3A and 3B, the reaction zone 100 further comprises pump-around loop 140.

Carbon monoxide and at least one reactant are continuously fed by feed streams 101 and 102, respectively, to reactor 103. The reactant feed stream 102 may be supplied through one or more high pressure pumps (not shown). In some embodiments, the high pressure pumps operate at a discharge pressure that is greater than the operating pressure within reactor 103. In some embodiments, the high pressure pumps operate at a discharge pressure of 10 to 60 barg, preferably 15 to 55 barg. The reactant feed stream 102 may supply at least one reactant selected from the group consisting of methanol, methyl acetate, methyl formate, dimethyl ether, and/or mixtures thereof, to the reactor 103. In preferred embodiments, the reactant feed stream 102 may supply methanol and methyl acetate. Optionally, the reactant feed stream 102 may be connected to one or more vessels (not shown) that store fresh reactants for the carbonylation process. In addition, although not shown there may be a methyl iodide storage vessel and/or catalyst vessel connected to the reactor 103 for supplying fresh methyl iodide and catalyst as needed to maintain reaction conditions.

One or more recycle feed streams 125, preferably from the reaction zone 101 may be fed to reactor 103. Although one recycle feed stream is shown as stream 125, there may be multiple streams that are fed separately to reactor 103. In other embodiment, one or more recycle feed streams from the purification zone (not shown) may also be fed to reactor 103. The recycle feed streams may comprise the components of the reaction medium, as well as residual and/or entrained catalyst and acetic acid. Optionally, there may be at least one fresh water stream (not shown) that may be fed to reactor 103.

In a preferred embodiment reactor 103 is a liquid phase carbonylation reactor. The reactor 103 is preferably either a stirred vessel or bubble-column type vessel, with or without an agitator, within which the reacting liquid or slurry contents are maintained, preferably automatically, at a predetermined level, which preferably remains substantially constant during normal operation. Into reactor 103, fresh methanol from feed stream 102, carbon monoxide feed stream 101, and recycle streams 125, along with optional methyl iodide streams, catalyst streams, and/or water streams, are continuously introduced as needed to maintain at least a water concentration of from 0.1 wt % to 14 wt. % in the reaction medium.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. A gaseous purge stream 106 is vented from the reactor 103 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Gaseous purge stream 106 may be scrubbed with acetic acid and/or methanol in recovery unit 104 to recover low boiling components. The gaseous purge stream 106 may be condensed and fed to a recovery unit 104 which may return low boiling components 108 to the top of reactor 103. The low boiling components 108 may comprise methyl acetate and/or methyl iodide. Carbon monoxide in the gaseous purge stream 106 may be purged in line 107 or fed via line 107' to base of flasher 120 to enhance rhodium stability.

Carbonylation product is drawn off from the carbonylation reactor 103 at a rate sufficient to maintain a constant level therein and is provided to a flasher 120 via stream 105. In flasher 120, the carbonylation product separates in a flash separation step with or without the addition of heat to obtain a crude product stream 122 comprising acetic acid, and a liquid recycle stream 123. The liquid recycle stream 123 comprises a catalyst-containing solution which preferably is recycled to the reactor via stream 125 using reactor recycle pump 121. In some embodiments, reactor recycle pump 121 operates at a discharge pressure that is greater than the operating pressure within reactor 103. In some embodiments, reactor recycle pump 121 operates at a discharge pressure of 10 to 60 barg, preferably 15 to 55 barg. The catalyst-containing solution predominantly contains acetic acid, the rhodium catalyst, and the iodide salt, along with lesser quantities of methyl acetate, methyl iodide, and water, as discussed above. The crude product stream 122 comprises acetic acid, methyl iodide, methyl acetate, water, methanol, and PRC's. The crude product stream 122 from flasher 120 is directed to a purification zone (not shown) for further separation and purification.

A purification zone (not shown) for use with the present invention may comprise a light ends column, a drying column, one or more columns for removal of PRC's, guard beds, vent scrubbers/absorbers, and/or heavy ends columns. The PRC removal columns are described in U.S. Pat. Nos. 6,143, 930, 6,339,171, and 7,223,886, and U.S. Publication Nos. 2005/0197513, 2006/0247466, and 2006/0293537, the entire contents and disclosures of which are hereby incorporated by reference. Guard beds are described in U.S. Pat. Nos. 4,615, 806, 4,894,477, and 6,225,498, the entire contents and disclosures of which are hereby incorporated by reference.

In one embodiment, the reactant may be fed from a fresh source, such as the feed source for the carbonylation reactor. In FIG. 1A, the fresh reactant from the reactant feed stream 102 is fed via line 124 to flasher 120. In optional embodiments, stream 124 may be obtained from a separate source of reactants than the feed stream 102 for the reactor 103. In one embodiment, a portion of the reactants is fed to a lower portion of flasher 120 via stream 124. Preferably stream 124 is cooled to a temperature of less than 60° C., e.g., less than 40° C. or less than 30° C. Cooling stream 124 may advantageously allow an increased flow rate through the reactor recycle pump 121, by net marginally cooling the entire liquid recycle stream 123 and improving the net positive suction head available (NPSHa) to pump suction.

In some embodiments, stream 124 is fed to flasher 120 at a point below where carbonylation product stream 105 enters the flasher. Preferably, stream 124 enters flasher 120 at a point below the surface of the liquid contained within the flasher 120, similar to the line 107' from the recovery unit 104. This may allow the contents of stream 124 to adiabatically mix with the liquid recycle in stream 123 without being carried over into the vapor crude product stream 122 sent to the purification zone. The resulting streams are combined in the flasher 120, directed to reactor recycle pump 121 via stream 123, and are directed back to reactor 103 via recycle stream 125.

In terms of weight percentage, the amount (rate) of reactants added to the base area of the flasher 120 may be from 0.01 wt. % to 20 wt % of the total flow rate of the liquid exiting the base of the flasher 120, and more preferably from 0.5 wt. % to 8 wt. %. In terms of the reactants fed to the reaction zone 100, the weight percentage of reactants fed to the flasher 120 may be from 0.1% to 50% of the total amount of reactants fed to the reaction zone 100 and more preferably from 0.1% to 25%.

Fresh reactants may also be fed to the liquid recycle stream 123 via line 124 as shown in FIG. 2A. Preferably stream 124 is fed to the liquid recycle stream 123 at a point upstream from reactor recycle pump 121. The resulting stream is fed back to reactor 103 via recycle stream 125. Preferably, when fresh reactants are added via line 124, the fresh reactants are added to the liquid recycle stream 123. Preferably, the fresh reactants are added to the liquid recycle stream 123 upstream of reactor recycle pump 121. In terms of weight percentage the amount of reactants added to the liquid recycle stream 123 may be from 0.1 wt. % to 20 wt. % of the total weight of the liquid recycle stream 123, and more preferably from 1 wt. % to 10 wt. %. In terms of the reactants fed to the reaction zone 100, the weight percentage of reactants fed to the liquid recycle line 123 may be from 0.1% to 50% of the total amount of reactants fed to the reaction zone 100 and more preferably from 0.1% to 25%.

Although one liquid recycle stream 123 and reactor recycle pump 121 is shown in FIG. 2A, in some embodiments, there may be multiple liquid recycle streams and/or pumps 121. For example, a portion of the liquid recycle stream may be separated and returned to the reactor via a secondary high total dynamic head (TDH) pump. The reactants may be fed to the separated portion of the liquid recycle stream.

In another embodiment, the fresh reactants may also be fed to a pump-around loop 140 as shown in FIG. 3A. A portion of stream 105 is directed to a pump 141, wherein the portion is returned to the reactor 103. Pump-around loop 140 may also comprise one or more heat exchangers. In one embodiment, pump-around loop may control the heat of the exothermic carbonylation reaction. In FIG. 3A, fresh reactants via line 124 may be added to any portion of the pump-around loop 140, but are preferably added downstream of the pump 141 to prevent the reactants, in particular methanol, from flashing in the pump suction of the pump-around loop 140. Pump 141 may be a low total dynamic head pump. In other embodiments, the pump-around loop may be connected to the reactor 103, such as those described in U.S. Pat. No. 7,465,823, which is incorporated by reference herein in its entirety. While not being bound to one particular theory, the introduction of reactants into the pump-around loop 140 increases the reaction activity with carbon monoxide in the loop, thereby increasing the energy in the pump-around loop that may be recovered via a heat exchanger (not shown) and directed to other locations within the acetic acid production process and/ or other processes.

In terms of weight percentage the amount of reactants added to the pump-around loop 140 may be from 0.05 wt. % to 5 wt. % of the total weight of the pump-around loop 140, and more preferably from 0.5 wt. % to 2 wt. %. In terms of the reactants fed to the reaction zone 100, the weight percentage of reactants fed to the pump-around loop 140 may be from 0.1 to 25% of the total amount of reactants fed to the reaction zone 100 and more preferably 0.5% to 20%.

In other embodiments, the reactants may be supplied as part of a processed stream, such as a recovery stream from a vent scrubber/absorber. Referring to FIGS. 1B, 2B and 3B, there is shown a vapor stream 131 that is captured by vent recovery unit 130 to produce a recovery stream 134 and a gaseous purge stream 133. A scrubbing solvent is fed to vent recovery unit 130 via stream 132. In one embodiment, the scrubbing solvent comprises at least one reactant selected from the group consisting of methanol, methyl acetate, methyl formate, dimethyl ether, and/or mixtures thereof. In one embodiment, the scrubbing solvent is taken from the fresh reactants fed to the reactor 103. Recovery stream 134 comprises a scrubbing solvent and low boiling point components, such as methyl iodide. In FIG. 1B recovery stream 134 is fed to flasher 120 as described above in FIG. 1A. Recovery stream may also be fed to liquid recycle stream 123 as shown in FIG. 2B similar to FIG. 2A. In addition, recovery stream may also be fed to pump-around loop 140 as shown in FIG. 3B similar to FIG. 3A.

Of course it should be understood that fresh reactants as well as reactants in the recovery stream may be co-fed upstream of the reactor recycle pump 121 and/or to the pump-around loop. For example, fresh reactants comprising methanol may be fed to the flasher as shown in FIG. 1A and combined with a recovery stream that comprises methanol that is fed to the liquid recycle stream as shown in FIG. 2B.

Although only one vapor stream 131 is shown, a process of the present invention may comprise one or more vapor streams. The one or more vapor streams 131 may be taken from any place in the system, including, but not limited to, reaction zone 100 or the purification zone. In the purification zone there are several locations that produce a vapor stream that may be scrubbed. These locations include the light ends column, PRC removal system, heavy ends column, and drying column, as well as decanters, overhead receivers, and storage vessels.

In some embodiments, the scrubbing solvent is chilled to a temperature of less than 25° C. prior to being fed into vent recovery unit 130, and preferably less than 20° C. The recovery stream 134 preferably has a temperature that is less than 40° C., e.g., less than 30° C. or less than 25° C. While not being bound to any particular theory, feeding at least one reactant at a temperature of less than 40° C. to the flasher liquid recycle stream, aids to stabilize the catalyst present in solution in the destination stream. In one embodiment, recovery stream 134 is added upstream of the reactor recycle pump 121 to cool the liquid recycle stream 123.

One of ordinary skill in the art having the benefit of this disclosure can design and operate the distillation columns described herein to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid, comprising the steps of:
reacting carbon monoxide with at least one carbonylatable reactant in a reactor containing a reaction medium to produce a reaction product comprising acetic acid, wherein the reaction medium comprises water, acetic acid, methyl acetate, a halogen promoter, and a catalyst;
separating the reaction product in a flasher into a liquid recycle stream and a crude product stream comprising acetic acid, the halogen promoter, methyl acetate and water;
introducing at least a portion of the liquid recycle stream to the reactor via one or more pumps; and
feeding a portion of the at least one reactant upstream of at least one of the one or more pumps;
wherein the liquid recycle stream comprises the at least one reactant, wherein the at least one reactant is selected from the group consisting of methanol, methyl acetate, methyl formate, dimethyl ether, and mixtures thereof.

2. The process according to claim 1, wherein the portion of the at least one reactant is fed to a lower portion of the flasher.

3. The process according to claim 2, wherein the lower portion of the flasher is below where the reaction product is fed to the flasher.

4. The process according to claim 1, wherein the portion of the at least one reactant is fed to the liquid recycle stream.

5. The process according to claim 1, wherein the portion of the at least one reactant fed to upstream of the pump is from 0.1 wt % to 50 wt % of the at least one reactant fed to the reactor.

6. The process according to claim 1, furthering comprising cooling the portion of the at least one reactant prior to feeding upstream of the one or more pumps to a temperature of from 10° C. to 30° C.

7. The process according to claim 1, wherein the at least one reactant is methanol.

8. The process according to claim 1, wherein the process further comprises:
capturing one or more vapor streams in a vent recovery unit;
scrubbing the one or more vapor streams with a scrubbing solvent comprising the at least one reactant to produce a recovery stream; and
feeding at least a portion of the recovery stream upstream of at least one of the one or more pumps.

9. The process according to claim 1, further comprising;
withdrawing a portion of the reaction product to a pump-around loop; and
feeding another portion of the at least one reactant to the pump-around loop.

10. A process for producing acetic acid, comprising the steps of:
reacting carbon monoxide with at least one carbonylatable reactant in a reactor containing a reaction medium to produce a reaction product comprising acetic acid, wherein the reaction medium comprises water, acetic acid, methyl acetate, a halogen promoter, and a catalyst;
withdrawing a portion of the reaction product to a pump-around loop comprising one or more heat exchangers; and
feeding at least one carbonylatable reactant to the pump-around loop.

11. The process according to claim 10, wherein the portion of the at least one reactant fed to the pump-around loop is from 0.5 wt % to 20 wt % of the at least one reactant fed to the reactor.

12. The process according to claim 10, wherein the at least one reactant is methanol.

13. The process according to claim 10, wherein the process further comprises:
- capturing one or more vapor streams in a vent recovery unit;
- scrubbing the one or more vapor streams with a scrubbing solvent comprising the at least one reactant to produce a recovery stream; and
- feeding at least a portion of the recovery stream to upstream of at least one of the one or more pumps.

* * * * *